US00PP30068P2

(12) United States Plant Patent
Barth et al.

(10) Patent No.: US PP30,068 P2
(45) Date of Patent: Jan. 8, 2019

(54) ***ILEX* PLANT NAMED 'GLORIE DWARF'**

(50) Latin Name: *Ilex crenata*
Varietal Denomination: Glorie Dwarf

(71) Applicant: Van Vliet New Plants B.V., Stroe (NL)

(72) Inventors: Reinhold Dirk Hinrikus Barth, Bad Zwischenahn (DE); Hinrikus Barth, Bad Zwischenahn (DE)

(73) Assignee: VAN VLIET NEW PLANTS B.V., Stroe (NL)

( * ) Notice: Subject to any disclaimer, the term of this patent is extended or adjusted under 35 U.S.C. 154(b) by 11 days.

(21) Appl. No.: 15/731,307

(22) Filed: May 22, 2017

(51) Int. Cl.
*A01H 5/00* (2018.01)

(52) U.S. Cl.
USPC ..... Plt./247

(58) Field of Classification Search
USPC ..... Plt./226, 247
See application file for complete search history.

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of *Ilex crenata* plant named 'Glorie Dwarf' that is characterized by its very compact plant habit, slow-growing growth habit and leaves that are small in size.

2 Drawing Sheets

Botanical classification: *Ilex crenata.*
Variety denomination: 'Glorie Dwarf'.

CROSS REFERENCE TO A RELATED APPLICATION

This application is related to a European plant breeders' rights application filed on Dec. 20, 2010, application No. 2010/2854. There have been no offers for sale anywhere in the world more than one year prior to the filing of this Application and no accessibility to one of ordinary skill in the art could have been derived from the printed plant breeder's rights documents.

BACKGROUND OF THE INVENTION

The present invention relates to a new and distinct cultivar of *Ilex crenata* and will be referred to hereafter by its cultivar name, 'Glorie Dwarf'. 'Glorie Dwarf' is a new cultivar of Japanese holly grown for use as an ornamental landscape plant.

The new cultivar was discovered as a naturally-occuring branch mutation by the Inventors in Kayhauserfeld, Germany in August of 2002 of *Ilex crenata* 'Glory Gem' (not patented) that was growing outdoors in a production field.

Asexual propagation of the new cultivar was first accomplished by one of the Inventors using semi-hardwood stem cuttings in June of 2003 in Kayhauserfeld, Germany. Asexual propagation by semi-hardwood stem cuttings has determined that the characteristics of the new cultivar are stable and are reproduced true to type in successive generations.

SUMMARY OF THE INVENTION

The following traits have been observed repeatedly and represent the characteristics of the new cultivar. These attributes in combination distinguish 'Glorie Dwarf' as a unique cultivar of *Ilex.*

1. 'Glorie Dwarf' exhibits a very compact plant habit.
2. 'Glorie Dwarf' exhibits a slow-growing growth habit.
3. 'Glorie Dwarf' exhibits leaves that are small in size.

The parent plant, 'Glory Gem', differs from 'Glorie Dwarf' in being less vigorous, less compact and leaves that are larger in size. 'Glorie Dwarf' can be most closely compared to the *Ilex crenata* cultivar 'Convexa' (not patented) and 'Helleri' (not patented). 'Convexa' and 'Helleri' are similar to 'Glorie Dwarf' in plant shape and leaf color. 'Convexa' and 'Helleri' differ from 'Glorie Dwarf' in being more vigorous, and in having less compact plant habits and leaves that are larger in size and less convexed in aspect.

BRIEF DESCRIPTION OF THE DRAWINGS

The accompanying colored photographs illustrate the overall appearance and distinct characteristics of a five year-old plant of the new cultivar as field grown in Stroe, The Netherlands and placed in a container for the photographs.

The photograph in FIG. 1 provides a side view of the plant habit of 'Glorie Dwarf'.

Figure 1:
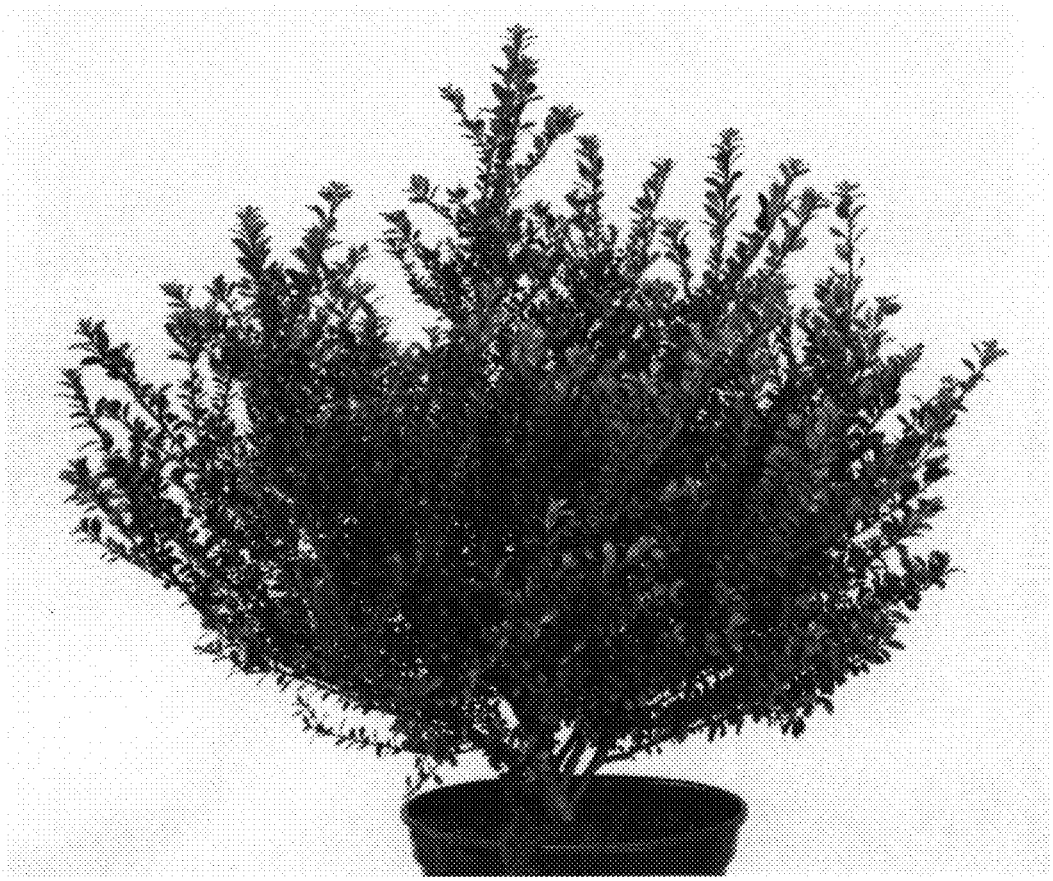
Figure 2:
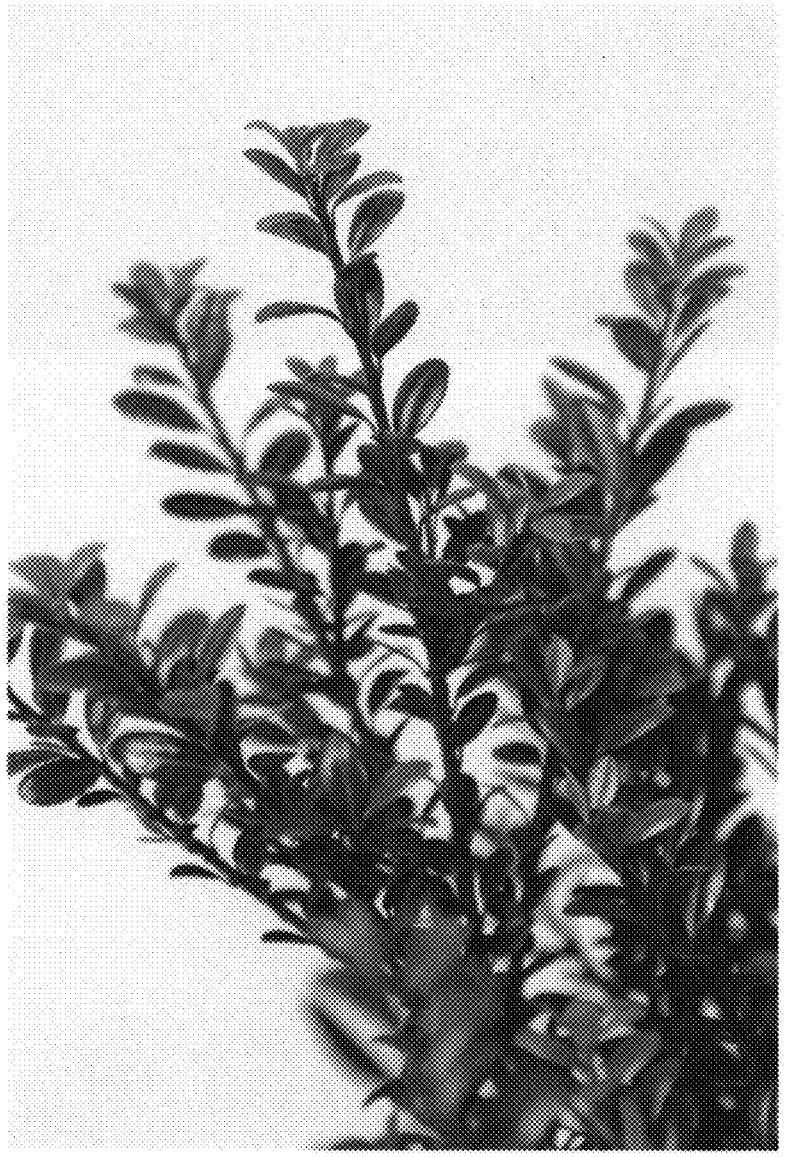

The photograph in FIG. 2 provides a view the foliage of 'Glorie Dwarf'.

The colors in the photographs may differ slightly from the color values cited in the detailed botanical description, which accurately describe the colors of the new *Ilex.*

DETAILED BOTANICAL DESCRIPTION

The following is a detailed description of five-year-old plants of the new cultivar field grown outdoors in Stroe, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type.*—Evergreen, perennial shrub.

*Plant habit.*—Broadly spreading, upright, globular in shape.

*Height and spread.*—Reaches an average of 63.8 cm in height and 59.8 cm in width.

*Cold hardiness.*—At least to U.S.D.A Zone 6.

*Diseases.*—No susceptibility to diseases has been observed.

*Root description.*—Densely fibrous and 165C in color.

*Propagation.*—Semi-hardwood stem cuttings.

*Root development.*—An average of 45 days to intiate roots at 25° and and an average of 4 months to produce a fully rooted cutting.

*Growth rate.*—Moderate.

Stem description:

*Branching.*—Freely branching; 10 main branches each with an average of 37 lateral branches per main branch.

*Stem size.*—Main branches; average of 43.4 cm in length, 6 mm in diameter, lateral branches; 12.3 cm in length, 2 mm in diameter.

*Stem surface.*—Glabrous and matte.

*Stem shape.*—Round.

*Stem aspect.*—Lateral branches in an average angle of 45° to main branches.

*Stem strength.*—Very strong.

*Stem color.*—Young stems; 200B, lower side 148A to 148B, older stems; 148A.

*Internode length.*—Average of 4 mm.

Foliage description:

*Leaf shape.*—Obovate.

*Leaf division.*—Simple.

*Leaf base.*—Attenuate.

*Leaf apex.*—Rounded.

*Leaf fragrance.*—None.

*Leaf venation.*—Pinnate, upper and lower veins 146C in color.

*Leaf margins.*—Upper half of leaf blade is undeeply serrate, lower half is entire.

*Leaf arrangement.*—Alternate.

*Leaf aspect.*—Convexed downward and held at varying aspects; upright to horizontal to slightly downward.

*Leaf attachment.*—Petiolate.

*Leaf surface.*—Both sides glabrous and slightly leathery, upper side glossy, lower side very slightly glossy.

*Leaf size.*—Mature and young leaves; 1.3 cm in length, 7 mm in width.

*Leaf quantity.*—Average of 31 per lateral branch.

*Leaf color.*—Young leaves upper surface; 143A, young leaves lower surface; 144A, mature leaves upper surface; between N137A and 147A, mature leaves lower surface; 143A.

*Petioles.*—Average of 3 mm in length, 0.75 mm in diameter, 146B to 146C in color, glabrous surface.

Flower description: Blooms have not been observd to date.

It is claimed:

1. A new and distinct cultivar of *Ilex* plant named 'Glorie Dwarf' as herein illustrated and described.

* * * * *